United States Patent
McCullough

(10) Patent No.: US 7,795,239 B2
(45) Date of Patent: Sep. 14, 2010

(54) SACCHARIDE COMPOSITIONS AND METHOD OF USE

(75) Inventor: Ricky W McCullough, Foster, RI (US)

(73) Assignee: Mueller Medical International LLC, Nevis (KN)

( * ) Notice: Subject to any disclaimer, the term of this patent is extended or adjusted under 35 U.S.C. 154(b) by 1015 days.

(21) Appl. No.: 11/013,172

(22) Filed: Dec. 15, 2004

(65) Prior Publication Data

US 2005/0112213 A1 May 26, 2005

Related U.S. Application Data

(60) Continuation-in-part of application No. 08/205,383, filed on Mar. 4, 1994, now Pat. No. 5,447,918, which is a continuation-in-part of application No. 08/077,715, filed on Jun. 17, 1993, now abandoned, which is a division of application No. 07/919,740, filed on Jul. 27, 1992, now abandoned.

(51) Int. Cl.
*A61K 31/7024* (2006.01)
*A61K 31/4439* (2006.01)
*A61K 31/4172* (2006.01)

(52) U.S. Cl. ............... 514/53; 514/63; 514/390; 514/338; 514/400; 514/561; 514/574; 424/686; 424/687

(58) Field of Classification Search ............... 514/53, 514/63, 390, 338, 400, 561, 574; 424/686, 424/687

See application file for complete search history.

(56) References Cited

U.S. PATENT DOCUMENTS 5,447,918 A * 9/1995 McCullough ................. 514/53

OTHER PUBLICATIONS

Glassman et al Gastrointestinal Endoscopy of North America, Jan. 1994, 4(1), 23-27.*
Moody et al Current Problems in Surgery, 1991, 28(7), 489-495.*
Mackay et al. Mackay, I.R., Rosen, F.S. (2001) Autoimmune Diseases, New England Journal of Medicine, vol. 345, No. 5, p. 340-350.*
The Merck Manual (16th Edition, 1992, pp. 830-835, 1305 and 1369-1371.*
The Merck Index 1996, 12th edition, p. 7020.*

* cited by examiner

*Primary Examiner*—Shaojia Anna Jiang
*Assistant Examiner*—Ganapathy Krishnan
(74) *Attorney, Agent, or Firm*—Occhiuti, Rohlicek & Tsao LLP

(57) ABSTRACT

Saccharide compositions and methods of their use to (a) treat functional bowel disorders, (b) gastroesophageal reflux disease and (c) syndromes of nausea, vomiting and diarrhea in man and animals. Also disclosed are saccharide compositions and methods of their use to accelerate the healing of erosions and ulcerated wounds. These same saccharide compositions allow for co-administration and unimpeded uptake of medications traditionally self-adsorbed to saccharides.

11 Claims, No Drawings ions of matter comprising of a) functionalized carbohydrates such as sucralfate or sucrose octasulfate combined with b) one or more irritant-relieving agents which when used allows functionalized carbohydrates to bind to tissue at a

SACCHARIDE COMPOSITIONS AND METHOD OF USE

CROSS REFERENCE TO RELATED DISCLOSURE

This application is a continuation-in-part of application Ser No. 08/205,383, filed Mar. 4, 1994 and now U.S. Pat. No. 5,447,918 granted 1995 Sep. 5, which was a continuation-in-part of application Ser. No. 08/077,715, filed Jun. 17, 1993, now abandoned, and which was a division of application Ser. No. 07/919,740, filed on Jul. 27, 1992, now abandoned.

This application is a continuation-in-part of application Ser No. 08/205,383, filed Mar. 4, 1994 and now U.S. Pat. No. 5,447,918 granted 1995, Sep. 5, which was a continuation-in-part of application Ser. No. 08/077,715, filed Jun. 17, 1993, now abandoned, and which was a division of application Ser. No. 07/919,740, filed on Jul. 27, 1992, now abandoned.

BACKGROUND

There is a constant need in the pharmaceutical industry for improvements on formulations that enable enhanced healing or evaluations of clinical syndromes involving ulceration of epithelium, whether on mucosal surfaces or on epidermal surfaces. The primary improvement of previously reported agents is the use of specialized concentrations of functionalized carbohydrates and anti-irritants, preferably anti-inrritants of the group comprised of antacids, acid reducers, proton pump inhibitors and phytotherapeutical herbals, more preferably carboxylic acid type of antacids, most preferable oxalate, citrate, fumarate, succinate and malate. Functionalized carbohydrates include sucrose octasulfate and sucralfate.

Previously reported agents of U.S. Pat. No. 5,447,918, specifically Example 1 and Example 12 of that report, included sucrose octasulfate as the functionalized carbohydrates and was found in practice to have enhanced tissue adherence and coating when combined, as claimed in that report (claim 8 U.S. Pat. No. 5,447,918), with citrate. This observation was not limited to citrate but observed also with fumarate, succinate, malate, alpha-keto-gluturate, that is all Kreb's cycle acids (KCA).

In addition to this, combinations involving sucrose octasulfate or sucralfate formulated in accordance to Example 7 of the same report (U.S. Pat. No. 5,447,918) was noted to have unimpeded absorption of cimetidine, ranitidine, nizatidine and omeprazole from the gastrointestinal (GI) tract. Typically, when cimetidine, ranitidine, nizatidine or omeprazole are given with an antacid alone or given with sucralfate alone, the absorption of such compounds from the GI tract is diminished by 15-20% (Ref 24. J Clin Gastroenterl 12 Suppl 2: S54-63, 1990). However, in practice agents combined in accordance to Example 7 formulation of U.S. Pat. No. 5,447, 918, showed no such dimunition of uptake, a novel characteristic, identified at that time and now claimed in this report.

Finally, combinations of sucrose octasulfate or sucralfate with KCA as formulated accordance to Example 8 formulation of U.S. Pat. No. 5,447,918 besides curing heartburn, also relieved nausea, vomiting and diarrhea in patients.

SUMMARY OF THE INVENTION

The present invention relates to novel pharmaceutical compositions of matter comprising of a) functionalized carbohydrates such as sucralfate or sucrose octasulfate combined with b) one or more irritant-relieving agents which when used allows functionalized carbohydrates to bind to tissue at a higher than usual concentration and permits concomitant uptake of cimetidine, ranitidine, nizatidine or omeprazole without interference to uptake.

Of particular note are compositions involving use of sucralfate or sucrose octasulfate with anti-irritants taken from a group that include 1) antacids, such as citrate, malate, magnesium hydroxide, calcium carbonate, malgadrate, glycine, magnesium carbonate, and other Kreb's cycle acids; 2) acid reducers like cimetidine, ranitidine, nizatidine, and famotidine; 3) proton pump inhibitors omeprazole, esomeprazole, pantoprazole, rabeprazole, and lansoprazole and 4) phytotherapeutic herbals like licorice, chamomile, saw palmetto, oryzonol, alginate, slippery elm bark.

The novelty of this invention is both the compositions as well as the method of use a) to improve potency of sucralfate, b) to permit concomitant administration of antacids compounds and proton pump inhibitors or histamine-2 blockers, and c) to relieve nausea, vomiting and diarrhea in patients who suffer from erosive as well as non-erosive gastroesophageal reflux syndrome (GERD).

COMPOSITIONAL CONCENTRATIONS OF COMPONENTS

The composition of this invention is in either liquid or solid dose form specifically formulated such that the weight/weight ratio for functionalized carbohydrates like sucralfate and sucrose octasulfate and the epigastralgic-relieving agents listed would range respectively from 10:1 to 1:10, preferably 5:1 to 1:6, most preferably 3:1 to 1:6 in either liquid or solid dose form. The anti-irritant relieving agents are one or more of the following group that include 1) antacids, such as citrate, malate, magnesium hydroxide, calcium carbonate, malgadrate, glycine, magnesium carbonate, Kreb's cycle acids 2) acid reducers like cimetidine, ranitidine, nizatidine, and famotidine3) proton pump inhibitors omeprazole, esomeprazole, pantoprazole, rabeprazole, and lansoprazole and 4) phytotherapeutic herbals like licorice, chamomile, saw palmetto, oryzonol, alginate, slippery elm bark.

Of course the anti-irritant role of antacid group is threefold. One purpose is to produce immediate neutralization of acid. A second purpose is to elevate the potency of functionalized poly/disaccharides, namely sucralfate and sucrose octasulfate, by promoting hydrogen-bonded and metal chelated polymerization of sucralfate or sucrose octasulfate in solution, which in turn when administered either orally or topically on ulcerated epithelial surfaces, higher concentrations of the functionalized poly/disaccharide would be achieved. This occurred when combining Kreb's cyle acids with sucralfate or sucrose octasulfate at weight to weight ratio 1:2 to 1:5. The third purpose is to mutually distract the antacid compounds and sucralfate or sucrose octasulfate compounds from electrostatic adsorption of concomitantly administered drugs. When both the antacid and sucralfate or sucrose octatasulfate are present between weight to weight ratios of 1:2 to 1:5 [antacid to sucralfate or sucrose octasulfate], the concomitantly administered acid reducers and proton pump inhibitors do not adsorb to either the antacid or to sucralfate or sucrose octatsulfate, thus remaining free in solution for uptake into the bloodstream from the GI tract.

The role of the acid reducers and proton pump inhibitors is to provide prolonged reduction in the hydrocholoric acid irritant in the GI tract. The role of the phytotherapeutic herbals is to improve the mucus gel barrier in the GI tract and to diminish inflammation on ulcerated epithelium.

ILLUSTRATION OF THE INVENTION

The following examples of this invention listed below are illustrative only; they are not at all intended to limit the scope of the invention, but rather to exemplify the practicality of this invention. These examples depict potential embodiments. The preferred embodiment of a poly[phosphoryl/sulfon]-ated carbohydrate-containing composition are those which contain sucralfate or sucrose octasulfate. It should be borne in mind, however, that other carbohydrate poly[phosphoryl/sulfon]-ates could be used as well. Additionally that the use of KCA's such as citrate, fumarate, succinate, oxalate, malate or alpha keto glutarate could be substituted with compounds that replace the carboxylate groups with carbamide, phosphonic, phosphate or even sulfonic, sulfonate substituents.

The following examples illustrate formulations wherein in the invention acts as a surface active high potency anti-irritant material.

EXAMPLE 1

Liquid Formulation

| Ingredients | mg/5 ml |
| --- | --- |
| Sucralfate or Sucrose Octasulfate | 250-500 |
| Methyl Paraben USP | 5-10 mg |
| Propyl Paraben USP | 5-10 mg |
| Citrate, fumarate, succinate or Malate | 100-175 mg |
| Magnesium Hydroxide | 175 mg |
| Calcium Carbonate | 175 mg |
| Xanthum Gum | 50 mg |
| Starch | 50 mg |
| Sodium Saccharin | 3.0-5.0 |
| Sorbitol USP | 200-350 mg |
| Flavor | q.s. |
| Water | 5.0 ml |

EXAMPLE 2

Liquid Formulation with Special Emulsion Formula

| Ingredients | mg/5 ml |
| --- | --- |
| Sucralfate or Sucrose Octasulfate | 250-500 |
| Methyl Paraben USP | 5-10 mg |
| Propyl Paraben USP | 5-10 mg |
| Citrate, Fumarate, Succinate or Malate | 100-175 mg |
| Simethecone | 40-80 |
| Calcium Carbonate/Magnesium Hydroxide | 180 mg/150 mg |
| Sodium Saccharin | 3.0-5.0 |
| Starch | 50-200 mg |
| Xanthum Gum | 50 mg |
| Sorbitol USP | 200-350 mg |
| Flavor | q.s. |
| Water | 5.0 ml |

In this example the xanthum gum and starch and sucrose octasulfate are in weight ratios vary from 1:1:10 to 1:4:8 and provide for an emulsion that is particularly smooth to taste, less gritty and chaulky when using magnesium hydroxide. The increase concentration of starch in the presence of xanthum gum and sucrose octasulfate appear key.

EXAMPLE 3

Acid Reducer Formulation

| Ingredients | Weight |
| --- | --- |
| Sucralfate or Sucrose Octasulfate | 250-500 mg |
| Methyl Paraben USP | 5-10 mg |
| Propyl Paraben USP | 5-10 mg |
| Citrate, Fumarate, Succinate or Malate | 100-175 mg |
| Cimetidine, Ranitidine, Nizatidine or Famotidine | 20-400 |
| Calcium Carbonate | 175 mg |
| Sodium Saccharin | 3.0-5.0 |
| Sorbitol USP | 200-350 mg |
| Flavor | q.s. |
| Water | 5.0 ml |

EXAMPLE 4

Proton Pump Inhibitor Formulation

| Ingredients | Weight |
| --- | --- |
| Sucralfate or Sucrose Octasulfate | 250-500 mg |
| Methyl Paraben USP | 5-10 mg |
| Propyl Paraben USP | 5-10 mg |
| Citrate, Fumarate, Succinate or Malate | 100-175 mg |
| Omerprazole, Esomeprazole, Pantoprazole, Rabeprazole, and Lansoprazole | 10-40 |
| Calcium Carbonate | 175 mg |
| Xanthum Gum | 50 mg |
| Starch | 50 mg |
| Sodium Saccharin | 3.0-5.0 |
| Sorbitol USP | 200-350 mg |
| Flavor | q.s. |
| Water | 5.0 ml |

EXAMPLE 5

Phytotherapeutic Formulation

| Ingredients | Weight |
| --- | --- |
| Sucralfate or Sucrose Octasulfate | 250-500 mg |
| Methyl Paraben USP | 5-10 mg |
| Propyl Paraben USP | 5-10 mg |
| Citrate, Fumarate, Succinate or Malate | 100-175 mg |
| Licorice, Chamomile, Saw Palmetto, Oryzonol, Alginate, Slippery Elm Bark | 10-400 |
| Calcium Carbonate | 175 mg |
| Xanthum Gum | 50 mg |
| Starch | 50 mg |
| Sodium Saccharin | 3.0-5.0 |
| Sorbitol USP | 200-350 mg |
| Flavor | q.s. |
| Water | 5.0 ml |

Laboratory Illustration of Invention

Enhanced Sucralfate adherence/Potency

GI tract ulcers induced by ethanol in 12 laboratory rabbits was treated 1 day later by enteral administration of generic 10% sucralfate suspension (n=4), 10% sucralfate-aluminum hydroxide/magnesium hydroxide suspension (n=4) and Example 2 Formulation above (10% sucralfate) Sucralfate Antacid Suspension (n=4) at equal volumes. At 3 hours after administration, a 1 cm square section of GI tract were examined for the content of adherent aluminum both in the ulcer crater and in surrounding normal tissue. Concentration of adherent aluminum was assayed by atomic absorption spectroscopy then correlated to sucralfate concentration.

TABLE 1

Enhanced Sucralfate Potency/Adherence
SUCRALFATE CONCENTRATION ON G.I. LINING
Three Hours Following Administration

| GENERIC Sucralfate Suspension SUCRALFATE | | GENERIC Sucralfate-Antacid Suspension SUCRALFATE | | GASTRAFATE ™ EXAMPLE 2 FORMULATION Emulsified Suspension SUCRALFATE | |
|---|---|---|---|---|---|
| Conc $\mu g/cm^2$ on Normal GI Tract (n = 4) | Conc $\mu g/cm^2$ on Ulcerated GI Tract (n = 4) | Conc $\mu g/cm^2$ on Normal GI Tract (n = 4) | Conc $\mu g/cm^2$ on Ulcerated GI Tract (n = 4) | Conc $\mu g/cm^2$ on Normal GI Tract (n = 4) | Conc $\mu g/cm^2$ on Ulcerated GI Tract (n = 4) |
| 3.1 (+/−0.12) | 3.6 (+/−0.10) | 6.1 (+/−0.31) | 9.4 (+/−0.62) | 22.1 (+/−0.51) | 82.5 (+/−1.32) |

Example 2 Formulation, manufactured by Sterling Foster Pharmaceutical and Glen Copel Pharmaceutical USA marketed under trade name Gastrafate appear to concentrate on normal un-injured GI tract 6-7x's and 3-4x's greater than generic sucralfate suspension and sucralfate antacid suspension. Gastrafate concentrate on acid-injured GI tract 23×'s greater and 8-9x's greater than generic sucralfate suspension and sucralfate antacid suspension.

Similar results were seen using sucrose octasulfate instead of sucralfate.

Unimpeded Uptake of Acid Reducers

When given alone with either sucralfate or magnesium hydroxide/aluminum antacid, fifteen to twenty percent, 15-20%, of dissolved cimetidine, ranitidine, and famotidine was not absorbed from the GI tract into the blood stream. However when sucralfate or sucrose octasulfate was coadministered with magnesium hydroxide/aluminum hydroxide, this diminution of uptake of cimetidine and ranitidine disappeared. It appears sucralfate and antacid at a weight:weight ratio of 4:1 to 2:1 mutually distract each other thus allowing dissolved histamine-2 blockers to be freely absorbed from the GI tract.

TABLE 2

AUC for Cimetidine and Ranitidine With Sucralfate, Magnesium Hydroxide and Aluminum Hydroxide

| | AUC for Cimetidine | | AUC for Ranitidine |
|---|---|---|---|
| Cimetidine Alone | 54.3 | Ranitidine Alone | 55.2 |
| Sucralfate and Cimetidine | 42.2 | Sucralfate and Ranitidine | 43.5 |
| Sucralfate Magnesium Hydroxide, Aluminum Hydroxide (4:1) with Cimetidine | 49.8 | Sucralfate Magnesium Hydroxide, Aluminum Hydroxide (4:1) with Ranitidine | 51.3 |
| Sucralfate Magnesium Hydroxide, Calcium Carbonate, (2:1) with Cimetidine | 54.2 | Sucralfate Magnesium Hydroxide, Aluminum Hydroxide (2:1) with Ranitidine | 54.9 |

This phenomenon most likely occur with other co-administered compounds such as proton pump inhibitors, anti-microbials, anti-seizure drugs, and theophylline type products.

Clinical Illustration of Invention

In a double-blind, randomized placebo-controlled clinical trial of 50 patients, 16 with erosive GERD and 34 with non-erosive GERD, Example 2 Formulation was tested against placebo in the treatment of symptoms of GERD. Symptom relief included relief of chest pain, heartburn sensation, and acid regurgitation.

Unexpected and novel were the relief of nausea, the relief of vomiting and relief of diarrhea

TABLE 3

Effects of Gastrafate Suspension vs Placebo

| SYMPTOMS | Gastrafate Group | Maximum Difference Noticed | Placebo Group | Maximum Difference Noticed | Statistical Significance |
|---|---|---|---|---|---|
| Chronic Severe Heartburn | 3 months-2 years | | 3 mths-2 years | | |
| Number of Daily Episodes | 3 or more per day | | 3 or more per day | | |
| Number Completed Study | 26 | | 24 | | |
| Number with Erosive Disease | 8 | | 8 | | |
| Number with Non-erosive | 18 | | 16 | | |
| Relief of Heartburn | 77% (20/26) | In 3-4 days | 21% (5/24) | In 14-17 days | $p < 0.05$ |
| Relief of Acid Regurgitation | 71% (10/14) | In 6-8 days | 38% (5/13) | In 14-17 days | $p < 0.10$ |
| Relief of Chest Pain | 82% (9/11) | In 6-8 days | 50% (5/10) | In 14-17 days | $p < 0.04$ |
| Relief of Other Assoctd Symptoms [Nausea Vomiting Dysphagia] | 88% (14/16) | In 6-8 days | 53% (8/15) | In 14-17 days | $p < 0.08$ |
| Relief of Irregular Bowel Movements [Loose Stools] | 80% (21/26) | In 6-8 days | 30% (7/24) | In 14-17 days | $p < 0.05$ |

Conclusion and Scope of Invention

The invention is not limited to what is described in the above examples. It will be obvious to persons skilled in the art that alterations may be made without departing from the scope of this invention, which scope is defined by the following claims.

REFERENCES

1. Tarnawski, A. et al: The mechanism of protective, therapeutic and prophylactic actions of sucralfate. Scand J. Gastroenterol 22:7-13, 1987.
2. Koelz H. R.: Protective drugs in the treatment of gastroduodenal ulcer disease. Scand J. Gastroenterol 21[suppl 125]: 156-163, 1986.
3. Samloff, I. M.; O'Dell, C: Inhibition of peptic activity by sucralfate. Am J Med 79: [suppl 2c]: 15-18, 1985.
4. Stapleton G. N. et al: Sucralfate in the prevention of porcine experimental peptic ulceraton. Am J Med 86[suppl 6a]:21-22, 1989.
5. Orlando R. C. et al: Mucosal protection by sucralfate and its components in acid-exposed rabbit esophagus. Gastroenterol 93: 352-61, 1987.
6. Guth, P. H.: Mucosal coating agents and other nonantisecretory agents/Are they cytoprotective? Dig Dis Sci 32: 647-654, 1987.
7. Borrero, E. et al: Comparison of antacid and sucralfate in the prevention of gastrointestinal bleeding in patients who are critically ill. Am J Med 79[suppl 2c]: 62-64, 1985.
8. Physician's Desk Reference: Carafate Informational Insert.
9. Tarnawski A. et al: Effect of sucralfate on normal human gastric mucosa. Endoscopic, histologic, and ultrastructural assessment [abstr] Gastrointest Endosc 30:155, 1984.
10. Arguelles-Martin F.; Gonzalez-Fernandez F.; Gentiles M.: Sucralfate versus cimetidine in the treatment of reflux esophagitis in children. Am J Med 86[suppl 6a]:73-76, 1989.
11. Caille G. et al: Effects of food and sucralfate on the pharmacokinetics of naproxen and ketoprofen in humans. Am J Med 86(suppl 6a):38-44, 1989.
12. Konturek S. J. et al: Double blind controlled study on the effect of sucralfate on gastric progstaglandin formation and microbleeding in normal and aspirin treated man. Gut 27:1450-1456, 1986.
13. Hollander D. et al: Protective effect of sucralfate against alcohol-induced gastric mucosal injury in the rat. Macroscopic, histologic, ultrastructural and functional time sequence analysis. Gastroenterol 88:366-74, 1985.
14. Brooks W. S. et al: Sucralfate: Nonulcer Uses. Am J Gastroent 80(3): 206-209, 1985.
15. McCullough R. W.: Sucrose Octasulfate Aluminum Salt and Disaccharide Polysulfate metal salts as an pharmaceutic excipient to protect the GI tract from local irritants. PTO Disclosure Doc No. 267,317 Nov. 14, 1990.
16. Nagashima R. et al: Sucralfate, a basic aluminum salt of sucrose I. Behavior in gastroduodenal pH. Arzrsch/Drug Res 29(11):1668-76, 1979].
17. Schweitzer E. J. et al: Sucralfate prevents experimental peptic esophagitis in rabbits. Gastroenterol 88:611-19, 1985.
18. Nagashima R. Development and characteristics of sucralfate. J Clin Gastroenterol 3[suppl 2]:103-10, 1981.
19. Slomiany B. et al: In vivo inhibition of peptic degradation of porcine gastric mucus glycoprote in by sucralfate. Scand J. Gastroenterol 20: 857-60, 1985.
20. Murty V. L. N. et al: Effect of sucralfate on the viscosity and retardation of hydrogen ion diffusion by gastric mucus. Gastroenterol 88: 1985.
21. Tanghoj, H. et al: Effects of sucralfate and cholestyramine on bile acid absorption. Gastroenterol 88(5), May 1985.
22. Smyth R. D., Herczeg T. et al: Correlation of In Vitro and In Vivo Methodology for Evaluation of Antacids. J Pharm Sci 65(7): 1045-47, 1976.
23. Evreux M.: Sucralfate, Alginate & Antacid in treatment of Gastroesophageal reflux. Amer J Med 83(Suppl 3B):48, 1987.
24. Reynolds J C: The clinical importance of drug interations with antiulcer therapy. J Clin Gastroenterl 12 Suppl 2: S54-63, 1990.

I claim:

1. A method of increasing the surface concentration potency of a saccharide composition involving the combination of a (a) saccharide selected from a group consisting of sucralfate, sucrose octasulfate, sucrose octaacetate, slippery elm mucilage, poly-sulfonated sugars and poly-phosphorylated sugars with (b) a chelating agent and (c) a metal cation in a weight ratio for (a), (b) and (c) ranging from 28:2:1 to 2:1:1.

2. A saccharide composition involving the combination of (a) a saccharide selected from a group consisting of sucralfate, sucrose octasulfate, sucrose octaacetate, slippery elm mucilage, poly-sulfonated sugars and poly-phosphorylated sugars with (b) a chelating agent and (c) a metal cation in a weight ratio for (a), (b) and (c) ranging from 28:2:1 to 2:1:1.

3. The composition wherein a disaccharide or polysaccharide selected from a group consisting of sucrose, sucralfate, sucrose octasulfate, sucrose octaacetate, slippery elm mucilage, poly-sulfonated sugars is combined with a chelating agent and a metal cation in a weight ratio ranging from 8:1:1 to 2:1:1.

4. The composition of claim 1 or 2 wherein the chelating agent is selected from a group consisting of carboxylic acids.

5. The composition of claim 1 or 2 wherein the metal cation is selected from a group consisting of calcium, magnesium and aluminum.

6. A composition comprising of (a) sucralflite, sucrose octasulfate or sucrose octa-acetate is combined with (b) malate, and (c) calcium carbonate in a weight ratio that ranges from 8:1:1 to 2:1:1.

7. A composition comprising of sucralfate with malate, and magnesium hydroxide admixed in a preferred weight ratio of 4:1:1.

8. A composition comprising sucralfate with malate, and magaldrate admixed in a preferred weight ratio of 4:1:1.

9. A composition as recited in any one of claims 3-8 fluther containing a pharmaceutically effective amount of a proton pump inhibitor, histamine-2 blocker, acid reducer, licorice, chamomile, saw palmetto, oryzonol and alginate.

10. An emulsion composition containing magnesium hydroxide made smooth to the taste, less gritty and less chaullcy by combining xanthan gum, starch and sucrose octasulfate in weight ratios from 1:1:10 to 1:4:8.

11. A method of treating a disorder selected from the group consisting of (a) functional bowel disorders, (b) constipation, (c) ileus, (d) erosive, ulcerated or inflammatory gastrointestinal disorders, (e) oral mucositis, alimentary mucositis, (g) heartburn, reflux dyspepsia. or indigestion and (h) syndromes of nausea, colic, vomiting or diarrhea occurring in man and animal in need thereof comprising the administration to said man and animal an effective amount of a composition as recited in any one of claims 2-10.

* * * * *